(12) United States Patent
Trubey

(10) Patent No.: US 8,808,519 B2
(45) Date of Patent: Aug. 19, 2014

(54) MICROFLUIDIC DEVICE

(75) Inventor: Richard K. Trubey, Upland, CA (US)

(73) Assignee: Hamilton Sundstrand Space Systems International, Windsor Locks, CT (US)

( * ) Notice: Subject to any disclaimer, the term of this patent is extended or adjusted under 35 U.S.C. 154(b) by 253 days.

(21) Appl. No.: 13/325,435

(22) Filed: Dec. 14, 2011

(65) Prior Publication Data

US 2013/0153416 A1    Jun. 20, 2013

(51) Int. Cl.
   *G01N 27/453*    (2006.01)
   *G01N 27/403*    (2006.01)

(52) U.S. Cl.
   USPC ........................................... 204/600

(58) Field of Classification Search
   USPC ............................ 204/450, 451, 600, 601, 411
   See application file for complete search history.

(56) References Cited

U.S. PATENT DOCUMENTS

| | | | | |
|---|---|---|---|---|
| 4,680,268 | A * | 7/1987 | Clark, Jr. | 205/778 |
| 6,773,566 | B2 * | 8/2004 | Shenderov | 204/450 |
| 8,388,909 | B2 * | 3/2013 | Pollack et al. | 422/504 |
| 2007/0242105 | A1 * | 10/2007 | Srinivasan et al. | 347/63 |
| 2010/0032293 | A1 * | 2/2010 | Pollack et al. | 204/450 |

FOREIGN PATENT DOCUMENTS

WO    WO 2006138543 A1 * 12/2006 ................ B01L 3/00

OTHER PUBLICATIONS

Morf et al. "Performance of amperometric sensors based on multiple microelectrode arrays," Sensors and Actuators B 44 (1997), 538-541.*

Revzin et al. Glucose, lacate, and pyruvate biosensor arrays based on redox polymer/oxidoreductase nanocomposite thin-films deposited on photolithographically patterned gold microelectrodes, Sensors and Actuators B 81 (2002) 359-368.*
Trubey: Autonomous Microfluidic Electrochemical Biosensor Array (AMEBA) System for Detection of Biomarkers Relevant to Astrobiology and Medical Diagnosis, dated Sep. 26, 2011—9 pp.
Lindsay, et al.: Discrete Microfluidics with Electrochemical Detection, Analyst (2007), vol. 132, pp. 412-416.
Cooney et al.: Electrowetting droplet Microfluidics on a Single Planar Surface, Microfluid. Nanofluid. (2006), 2, pp. 435-446.
Kim et al.: Electronic-Nose for Detecting Environmental Pollutants: Signal Processing and Analog Front-End Design, Analog Integr. Circ. Sig. Process, dated Apr. 11, 2011—18 pp. [DOI 10.1007/s10470-011-9638-1].
Dubois, et al.: Ionic Liquid Droplet as e-Microreactor, Analytical Chemistry (2006), vol. 78, pp. 4909-4917.
Poulos, et al.: Electrowetting on Dielectric-based Microfluidics for Integrated Lipid Bilayer Formation and Measurement, Applied Physics Letters, dated Jul. 8, 2009—3 pp. [DOI: 10.1063/1.3167283].
Cho et al.: Creating, Transporting, Cutting, and Merging Liquid Droplets by Electrowetting-Based Actuation for Digital Microfluidic Circuits, Journal of Microelectromechanical Systems (2003), vol. 12, pp. 70-80.
Matysik: Miniaturization of Electroanalytical Systems, Anal Bioanal. Chem. (2003), vol. 375, pp. 33-35.

(Continued)

*Primary Examiner* — Alex Noguerola
(74) *Attorney, Agent, or Firm* — Carlson, Gaskey & Olds, P.C.

(57) ABSTRACT

A microfluidic device includes a micro-channel that defines a plane. A plurality of drive electrodes is located on a first side of the plane. At least one ground electrode is operable to establish an electric potential with the plurality of drive electrodes. An array of electrochemical biosensors is located on a second, opposite side of the plane.

25 Claims, 1 Drawing Sheet

(56) References Cited

OTHER PUBLICATIONS

Yeh, et al.: Nanoelectrodes for Biological Measurements, Advanced Review, 2010 John Wiley & Sons, Inc., vol. 2, Mar./Apr. 2010, pp. 176-188.

Malic, et al.: Integration and Detection of Biochemical Assays in Digital Microfluidic LOC Devices, Lab Chip (2010), vol. 10, pp. 418-431.

* cited by examiner

MICROFLUIDIC DEVICE

BACKGROUND

This disclosure relates to a microfluidic device and method for the chemical analysis of microfluid droplets.

Microfluidic devices based on "digital microfluidics" or electrowetting-on-dielectric (EWOD) are known and used for transporting microfluids. A conventional EWOD-based microfluidic device includes a bottom plate, a top plate and a channel between the plates for the fluid. The bottom plate includes multiple individually addressable control (drive) electrodes and the top plate includes a ground electrode. The control electrodes and the ground electrode cooperate to establish an electric potential. The control electrodes are individually turned on or off to establish an electric potential that influences movement of fluid within the channel. For example, the microfluidic device can divide a sample droplet into smaller droplets and mix droplets with selected reagents. The microfluidic device can also move the droplets to an analysis zone located near a transparent window for the purpose of conducting an optically based measurement using an external analysis device. Such a microfluidic device is commonly referred to as a "lab-on-a chip" system.

SUMMARY

Disclosed is a microfluidic device that includes a microchannel which defines a plane. A plurality of drive electrodes is located on a first side of the plane. At least one ground electrode is operable to establish an electric potential with the plurality of drive electrodes. An array of electrochemical biosensors is located on a second, opposite side of the plane.

In another aspect, a microfluidic device includes a first plate and a second plate that is spaced apart from the first plate such that there is a micro-channel between the first plate and the second plate. The first plate includes a plurality of drive electrodes and the second plate includes an array of electrochemical biosensors. At least one ground electrode is operable to establish an electric potential with the plurality of drive electrodes.

BRIEF DESCRIPTION OF THE DRAWINGS

The various features and advantages of the disclosed examples will become apparent to those skilled in the art from the following detailed description. The drawings that accompany the detailed description can be briefly described as follows.

DETAILED DESCRIPTION OF THE PREFERRED EMBODIMENT

Figure 1:
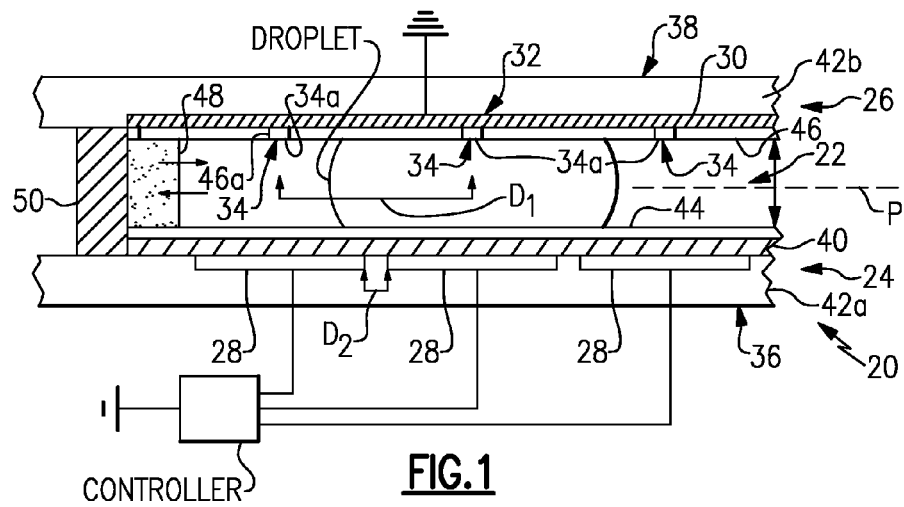
FIG. 1 shows a cross-section of a portion of an example microfluidic device.
Figure 2:
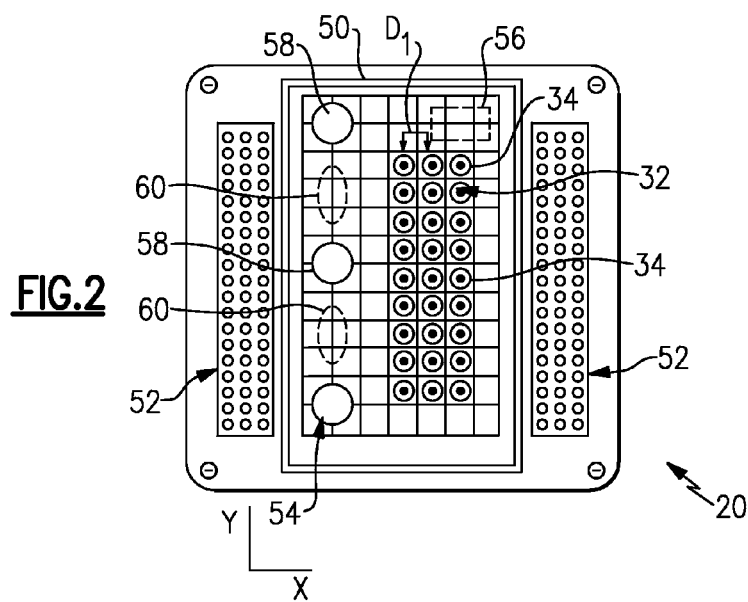
FIG. 2 shows a top view of the microfluidic device of FIG. 1.

FIG. 1 illustrates a portion of an example microfluidic device 20 and FIG. 2 shows a top view of the microfluidic device 20. As will be appreciated from the description and figures, the microfluidic device 20 is compact and can be reusable, enables rapid analysis and can be used for in situ detection of biological molecules in astrobiology, medical/health or other fields, for example.

As shown, the microfluidic device 20 includes a microchannel 22 that defines a plane P. In the plane P, the microchannel 22 extends in an X-direction and Y-direction (X-Y plane) such that sample droplets moving in the micro-channel 22 can move in both the X-direction and the Y-direction. The prefix "micro-" refers to the size of the depth dimension (perpendicular to the plane P) of the micro-channel 22 being 1000 micrometers or less. In further embodiments, the depth dimension is 500 micrometers or less.

In the example, the plane P bisects the micro-channel 22 and defines a first side 24 (below P in FIG. 1) and a second, opposite side 26 (above P in FIG. 1). A plurality of drive electrodes 28 is located on the first side 24 of the plane P. For example, the electrodes are conductive pads that are electrically connectable to a voltage source. At least one ground electrode 30 is operable to establish an electrical potential with the plurality of drive electrodes 28. An array 32 of electrochemical biosensors 34 is located on the second side 26 of the plane P.

In this example, the electrochemical biosensors 34 contain different biologically active materials 34a, such as immobilized enzymes, that are catalytically active with regard to different target analytes. For example, the selected biological materials 34a are immobilized within a polymeric (organic) or inorganic matrix or scaffold attached to an underlying electrode. Alternatively, the selected biological materials 34a are immobilized onto an electrode, thereby creating the electrochemical biosensors 34 via adsorption, covalent bonding, cross-linking with a bio-functional agent, affinity bonding or as a paste.

In one embodiment, the immobilized biological materials 34a are enzymes selected from oxidoreductase enzymes (oxidases, dehydrogenases, peroxidases, and oxygenases) or combinations thereof that catalyze oxidation reactions when in the presence of a target analyte contained in a sample to generate an electric current. Target analytes of interest include, but are not limited to, amino acids, carbohydrates, nucleobases, amines, amino sugars, aldehydes and other molecules (including polymers) containing these (or similar) functionalities.

In further embodiments, the immobilized enzymes are selected from L-amino acid oxidase, D-amino acid oxidase, alcohol oxidase, alcohol dehydrogenase, aldehyde dehydrogenase, amine oxidase, xanthine oxidase, glycerol dehydrogenase or other biologically derived materials that are effective to catalyze a reaction that generates an electric current. In additional embodiments, the immobilized enzymes include at least one of glucose oxidase or dehydrogenase enzymes requiring nicotinamide adenine dinucleotide or other coenzymes.

It is to be appreciated that the biological materials 34a can be selected to enable detection of other substances, including proteins and organisms, as well. In another embodiment, the immobilized biological materials 34a are selected to enable an immunoassay. In this example, the biological materials 34a are comprised of antigens or antibodies that participate in a sequence of steps automatically performed as part of a standard immunoassay method that uses an electrochemical label/reporter (usually involves an enzyme). Signal generation occurs by a mechanism similar to that employed by the embodiments that use immobilized enzymes directly to generate an electric current in the presence of a target analyte/organism contained in a sample. In further embodiments relevant to medical diagnostics, antibodies are selected to enable detection of pathogenic organisms (e.g., hepatitis, meningitis, Lyme's, influenza, anthrax, plague, smallpox, etc.) and proteins such as prostate-specific antigen and food toxins (e.g., staphylococcal enterotoxin B, botulinum toxin, etc.) in blood and other biological fluids. Pregnancy-specific markers and cardiac markers (e.g., cardiac troponin I, C-reactive protein, etc.) are additional examples of relevant target analytes. Given this description, one of ordinary skill in the art will recognize other types of biological materials 34a, including but not limited to enzymes, antigens, antibodies, and nucleic acids (including aptamers), that will benefit from this disclosure. In an immunoassay embodiment, the chemistry and reactions can be conducted using immobilized antigens or antibodies to comprise electrochemical biosensors 34 or the equivalent immobilization chemistry can be performed using magnetic beads in a known manner. Thus, the microfluidic device 20 can also be adapted with a permanent magnet or an electromagnet for influencing the position of droplets containing magnetic beads.

Each electrochemical biosensor 34 includes a plurality of electrodes (not shown) that serve to detect a target analyte. For example, each of the electrochemical biosensors 34 includes a working electrode, a reference electrode and an auxiliary electrode. Alternatively, one or all of the electrochemical biosensors 34 include only two electrodes, the working electrode and the auxiliary (or counter) electrode. The electrodes of the electrochemical biosensors 34 can include metallic material (for example, gold, platinum, indium tin oxide), metallic nanoparticles, carbon material, functionalized carbon nanotubes or combinations thereof, for example. Each of the biological materials 34a is immobilized on the working electrode of its respective electrochemical biosensor 34.

In the illustrated example, the micro-channel 22 extends between a first plate 36 and a second plate 38. The first plate 36 includes the plurality of drive electrodes 28 and the second plate includes the array 32 of electrochemical-based biosensors 34. Thus, the drive electrodes 28 and the electrochemical biosensors 34 are separated by the micro-channel 22, which reduces electrical interference between the drive electrodes 28 and the electrochemical biosensors 34.

Figure 3:
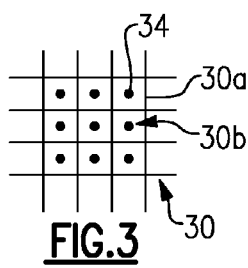
FIG. 3 shows a grid of ground trace wires in a microfluidic device.

In this example, the second plate 38 also includes the ground electrode 30, although the ground electrode 30 can alternatively be included in the first plate 36. In embodiments, the ground electrode 30 is a layer of electrically conductive material, such as indium tin oxide. In another example shown in FIG. 3, the ground electrode 30 includes a grid of lines or wires 30a of the electrically conductive material. Using the grid of lines or wires 30a provides areas 30b between the lines or wires 30a for easier placement of the electrochemical biosensors 34.

The first plate 36 also includes a dielectric layer 40 that extends over the drive electrodes 28. The dielectric layer 40 and the drive electrodes 28 are arranged on a first substrate 42a such that each drive electrode 28 is located between the first substrate 42a and the dielectric layer 40. For example, the dielectric layer 40 includes or is acrylic, polyimide, parylene or combinations thereof. The electrochemical biosensor 34 and ground electrode 30 are arranged on a second substrate 42b. In embodiments, the substrates 42a and 42b are individually selected from polymer/glass composites (for example, printed circuit board material), glass layers, and silicon layers. At least the second substrate 42b may be transparent glass or Mylar to permit observation of the sample within the microfluidic device 20.

The first plate 36 and the second plate 38 also include, respectively, a first hydrophobic surface 44 on the first side 24 and a second hydrophobic surface 46 on the second side 26. The hydrophobic surfaces 44 and 46 facilitate movement of sample droplets through the micro-channel 22. The second hydrophobic surface 46 includes a plurality of openings 46a that correspond in location to respective ones of the electrochemical biosensors 34 such that each of the openings 46a establishes fluid communication for electrochemical interaction between its respective electrochemical biosensor 34 and the micro-channel 22. Thus, the openings 46a permit sample droplets in the micro-channel 22 to be exposed to the electrochemical biosensors 34. Each of the openings 46a is substantially equal in area to the area of its corresponding electrochemical biosensor 34, to minimize the area that is not covered with the second hydrophobic surface 46. The openings 46a can be formed by masking during the deposition process of the second hydrophobic surface 46, mechanical removal laser lift-off, or oxygen plasma etching, for example.

In one embodiment, the hydrophobic surfaces 44 and 46 include a hydrophobic polymer composition. The composition may include a fluoropolymer, such as polytetrafluoroethylene. In other embodiments, the polymer includes silicone or fluorosilicone. In further examples, the composition includes additives for enhanced hydrophobicity.

Optionally, the microfluidic device 20 includes a hydrogel sorbent material 48 located within the micro-channel 22. The hydrogel composition may include polyvinyl alcohol, silicone, or acrylate polymers. In other embodiments, the sorbent includes silica gel. The sorbent material 48 is actively sorbent with regard to moisture such that the sorbent material 48 selectively captures and releases moisture into the micro-channel 22 to establish a predetermined moisture concentration in the micro-channel 22.

As shown in FIG. 2, a gasket 50 extends around the perimeter of the micro-channel 22 between the first plate 36 and the second plate 38 to seal the micro-channel 22 from the surrounding environment. Thus, the micro-channel 22 is bounded in an X-Y plane by the gasket 50. In embodiments, the gasket 50 is formed of an elastomer material, a metallic material (e.g., a braze metal) or an inorganic material.

The drive electrodes 28 and the electrochemical biosensors 34 are electrically connected to individual electrical contacts 52 that are subsequently connected to an external controller/sequencer, potentiostat, multiplexing electronics, other external voltage sources and/or the like for operating the microfluidic device 20. In this regard, the microfluidic device 20 includes no moving parts or onboard controls and voltage sources. Thus, the microfluidic device 20 is compact and can be incorporated as a component module into a larger assembly, such as a handheld analysis device, medical analysis kit or manned/unmanned space vehicle.

Figure 4:
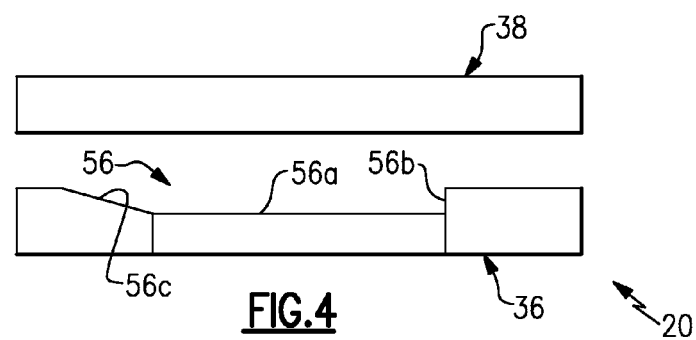
FIG. 4 shows a recessed well waste area of a microfluidic device.

The microfluidic device 20 further includes a sample port opening 54 that extends through at least one of the first plate 36 or the second plate 38 for the transfer or injection of a sample into the microfluidic device 20. Optionally, the microfluidic device 20 also includes a recessed well 56, as shown in FIG. 4, which serves as a waste collection area for used sample droplets. The recessed well 56 includes a hydrophobic bottom surface 56a and hydrophilic sidewalls 56b that extend partially around the perimeter of the bottom surface 56a and generally perpendicular to the bottom surface 56a. A sloped hydrophobic sidewall 56c extends around another portion of the bottom surface 56a and permits droplets to enter the recessed well 56 via the EWOD mechanism. The sloped hydrophobic sidewall 56c is at a transverse, non-perpendicular angle with regard to the bottom 56a and the hydrophilic sidewalls 56b. The sloped sidewall 56c and bottom surface 56a each contain a plurality of drive electrodes 28 and a grid of ground lines or wires 30a, to control droplet movement.

Because of the increased depth of the micro-channel 22 in the recessed well 56, the function associated with ground electrode 30 is included in the first plate 36 with the drive electrodes 30. Thus, in this region of the device it is not required that the droplet maintain contact with the second plate 38 in order to remain electrically grounded. In one embodiment, the hydrophilic sidewalls 56b include a hydrophilic polymer composition containing polyethylene glycol. The hydrophilic sidewalls 56b serve to hold waste sample droplets in the recessed well 56, where the droplets adhere to the hydrophilic material and eventually pool together.

Optionally, the microfluidic device 20 also includes one or more reagent zones 58 and mixing zones 60 that serve, respectively, for holding reagent materials and for mixing the reagent materials with samples. Reagents could include, but are not limited to, pH buffers, electrochemical labels, and enzymes that degrade polymeric species such as polypeptides or polysaccharides into smaller detectable species.

In operation (using an external controller and voltage source), a liquid sample is transferred via the sample port 54 into the microfluidic device 20. If the sample volume is initially larger than desired, the microfluidic device 20 can divide the sample using the drive electrodes 28 and ground electrode 30 to provide one or more discrete droplet samples of a desired size, such as a volume of approximately 0.1-20 microliters. In some examples, the microfluidic device 20 analyzes a plurality of sample droplets to obtain an averaged output analysis.

Depending on the sample, the microfluidic device 20 can mix the sample with a selected reagent from the reagent zone 58 prior to analysis. Alternatively, if mixing is unnecessary, the microfluidic device 20 can commence with the analysis. In this regard, the microfluidic device 20 provides enhanced sensitivity through direct analysis of a sample or sample/reagent rather than a sample that is diluted in a continuous flowing stream.

Upon commencement of the analysis, the microfluidic device 20 controls the drive electrodes 28 and ground electrode 30 to move the sample to one of the biosensors 34. As shown in FIG. 1, each electrochemical biosensor 34 is centered over one of the drive electrodes 28. The sample droplet tends to center over the activated drive electrode 28. By centering the electrochemical biosensors 34 over respective drive electrodes 28 the sample droplet centers under the corresponding electrochemical biosensor 34.

Once moved to a selected electrochemical biosensor 34, in general the biological materials 34a associated with that electrochemical biosensor 34 catalyze a reaction in the presence of a target analyte. If the target analyte is present in the sample, the catalysis reaction generates an electric current between the working electrode and the auxiliary electrode. The generated electric current serves as a signal to the controller that represents the presence of the target analyte in the sample. On the other hand, if the target analyte is not present in the sample, there is no catalysis reaction and no electric current. The absence of a signal represents the absence of the target analyte in the sample. However it is to be appreciated that if the device is configured to perform a competitive immunoassay, then the sensor signal decreases in the presence of target analyte. In this case a maximum signal level represents the absence of the target analyte in the sample.

Once an analysis is conducted using one of the electrochemical biosensors 34, the sample droplet can be moved to another one of the electrochemical biosensors 34 to test for the presence of a different target analyte. Thus, by using different biological materials 34a in the array 32 of electrochemical biosensors 34, the microfluidic device 20 can detect different target analyte species within a sample. After completion of the analysis, the sample droplet can be moved to the recessed well 56 waste area. Optionally, the microfluidic device 20 can be flushed with a cleaning solution after the analysis to remove any residual sample.

The microfluidic device 20 is also designed to be compact and for rapid analysis. In these regards, the array 32 of electrochemical biosensors 34 is arranged with a predetermined spacing distance $D_1$ (FIG. 1) between immediately neighboring electrochemical biosensors 34. For example, the spacing distance $D_1$ is from 0.8 to 1.65 millimeters. Similarly, the drive electrodes 28 define a spacing distance $D_2$ between immediately neighboring ones of the drive electrodes 28. The spacing distance $D_1$ and the spacing distance $D_2$ are selected to meet a predetermined scalable ratio of $D_1:D_2$. That is, the example ratios are scalable with regard to the dimensions $D_1$ and $D_2$. In one example, the scalable ratio of $D_1:D_2$ is from 4:1 to 33:1. The given scalable ratio ensures that the sample droplet is properly centered over a respective one of the drive electrodes 28 and is exposed to only a single one of the electrochemical biosensors 34. That is, the particular predetermined spatial relationship between the drive electrodes 28 and the electrochemical biosensors 34 ensures that the sample droplet is not exposed to more than a single one of the electrochemical biosensors 34 at a time. Thus, even if the microfluidic device 20 is scaled up or down, as long as the spacing distances $D_1$ and $D_2$ are within the given scalable ratio range, the sample droplet will be properly positioned over a given one of the drive electrodes 28 for exposure to only a single one of the electrochemical biosensors 34, while also providing a compact packing of the electrochemical biosensors 34.

In further embodiments, the scalable ratio is from 6:1 to 18:1 or 9:1 to 13:1. In addition to ensuring that the sample droplet is exposed to only a single one of the electrochemical biosensors 34, these example ratios provide for a compact arrangement.

In another embodiment, the envelope size of each of the electrochemical biosensors 34 and of each of the drive electrodes 28 is preselected for proper operation of the microfluidic device 20. For example, the envelope size of each electrochemical biosensor 34 and of each drive electrode 28 is represented by the projected area in the X-Y plane (plane P) of the micro-channel 22. Thus, each electrochemical biosensor 34 and each drive electrode 28 define a footprint area. In the illustrated example, the footprint area of each of the electrochemical biosensors 34 is less than the footprint area of each of the drive electrodes 28. Using a smaller footprint area for the electrochemical biosensors 34 reduces or eliminates electrical interference between the electrochemical biosensors 34 and the drive electrodes 28. In a further embodiment, a scalable ratio of the footprint area of the electrochemical biosensor 34 to the footprint area of the drive electrode 28 is 1:9 or less.

The array 32 of electrochemical biosensors 34 is also designed to be compact and facilitate rapid analysis. For example, the array 32 has a packaging density of the electrochemical biosensors 34 of about 0.4 sensors/mm$^2$ or greater, or about 0.9 sensors/mm$^2$ or greater.

As shown in FIG. 2, the array 32 includes a plurality of rows of the electrochemical biosensors 34. In operation, areas of the microfluidic device 20 where there are no electrochemical biosensors 34 can be used to "park" sample droplets as a time delay while other droplets are analyzed or to allow a reaction to proceed, for example. Alternatively, additional paths for transport or "parking" can be provided with no electrochemical biosensors 34. The additional paths can be around the electrochemical biosensors 34 or within the array 32.

In one example, the rows are designed to detect different classes of target analytes. For example, the biological materials 34a of the electrochemical biosensors 34 in one of the rows are selected to detect a first class of target analyte and the biological materials 34a of the electrochemical biosensors 34 in another of the rows are selected to detect a second, different class of target analyte. For instance, one row can be directed to detecting L-amino acids and another row can be directed to detecting D-amino acids, amines, aldehydes, or other class of targeted analytes.

Additionally, the electrochemical biosensors 34 of each individual row can include biological materials 34a that are selected to progressively identify a targeted analyte. For instance, a first one of the electrochemical biosensors 34 in a row can include a biological material 34a for detection of the general class of target analyte (for example, L-amino acids). Each subsequent electrochemical biosensor 34 in the row can include a biological material 34a that is selected to detect a specific type of the general target analyte (for example, various individual L-amino acids). Thus, the rows and electrochemical biosensors 34 are arranged for efficient analysis and to reduce the distance that a sample droplet has to be moved for analysis.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A microfluidic device comprising:
a micro-channel defining a plane;
a plurality of drive electrodes located on a first side of the plane, the drive electrodes being arranged in side-by-side rows;
at least one ground electrode operable to establish an electric potential with the plurality of drive electrodes; and
an array of electrochemical biosensors located on a second, opposite side of the plane, the electrochemical biosensors being arranged in side-by-side rows.

2. The microfluidic device as recited in claim 1, wherein the micro-channel extends between a first hydrophobic surface on the first side and a second hydrophobic surface on the second side.

3. The microfluidic device as recited in claim 1, wherein each electrochemical biosensor and each of the plurality of drive electrode defines a respective footprint area, and the footprint area of each of the electrochemical biosensors is less than the footprint area of each of the plurality of drive electrodes.

4. The microfluidic device as recited in claim 1, including a spacing distance between immediately neighboring ones of the electrochemical biosensors of 0.8-1.65 millimeters.

5. The microfluidic device as recited in claim 1, wherein each electrochemical biosensor is centered over a respective one of the plurality of drive electrodes.

6. The microfluidic device as recited in claim 1, including a sorbent material located within the micro-channel, the sorbent material being actively sorbent with regard to moisture.

7. The microfluidic device as recited in claim 1, wherein the side-by-side rows of electrochemical biosensors are parallel to each other and the side-by-side rows of drive electrodes are also parallel to each other.

8. The microfluidic device as recited in claim 1, wherein the electrochemical biosensors that are arranged in the side-by-side rows of electrochemical biosensors have a one-for-one correspondence to the drive electrodes that are arranged in the side-by-side rows of drive electrodes.

9. The microfluidic device as recited in claim 1, wherein a scalable ratio of a footprint area of one of the electrochemical biosensors to a footprint area of one of the drive electrodes is 1:9 or less.

10. The microfluidic device as recited in claim 1, wherein the electrochemical biosensors of one of the side-by-side rows of electrochemical biosensors are configured to progressively identify a target analyte.

11. The microfluidic device as recited in claim 1, wherein one of the side-by-side rows of electrochemical biosensors includes a first electrochemical biosensor configured to detect a general class of target analyte and subsequent electrochemical biosensors are configured to detect, respectively, specific types of the general class of target analyte.

12. The microfluidic device as recited in claim 1, wherein the side-by-side rows of electrochemical biosensors are configured, by row, to detect different classes of target analytes.

13. A microfluidic device comprising:
a micro-channel defining a plane;
a plurality of drive electrodes located on a first side of the plane;
at least one ground electrode operable to establish an electric potential with the plurality of drive electrodes; and
an array of electrochemical biosensors located on a second, opposite side of the plane, wherein the micro-channel extends between a first hydrophobic surface on the first side and a second hydrophobic surface on the second side, and wherein the second hydrophobic surface includes a plurality of openings each corresponding in location to a respective one of the electrochemical biosensors such that each of the openings establishes fluid communication between its respective electrochemical biosensor and the micro-channel.

14. The microfluidic device as recited in claim 13, wherein each of the electrochemical biosensors includes a different immobilized biological material.

15. The microfluidic device as recited in claim 14, wherein the immobilized biological materials include at least one of antigens or antibodies.

16. The microfluidic device as recited in claim 14, wherein the immobilized biological materials include enzymes.

17. The microfluidic device as recited in claim 16, wherein the immobilized enzymes include an oxidoreductase enzyme.

18. The microfluidic device as recited in claim 13, including a first spacing distance $D_1$ between immediately neighboring ones of the electrochemical biosensors and a second spacing distance $D_2$ between immediately neighboring ones of the drive electrodes such that a scalable ratio of $D_1:D_2$ is from 4:1 to 33:1.

19. The microfluidic device as recited in claim 18, wherein the scalable ratio is from 6:1 to 18:1.

20. The microfluidic device as recited in claim 18, wherein the scalable ratio is from 9:1 to 13:1.

21. A microfluidic device comprising:
a first plate; and
a second plate spaced apart from the first plate such that there is a micro-channel between the first plate and the second plate,
the first plate including a plurality of drive electrodes,
the second plate including an array of electrochemical biosensors, and
one of the first plate or the second plate includes at least one ground electrode operable to establish an electric potential with the plurality of drive electrodes, including a first spacing distance $D_1$ between immediately neighboring ones of the electrochemical biosensors and a second spacing distance $D_2$ between immediately neighboring ones of the plurality of drive electrodes such that a scalable ratio of $D_1:D_2$ is from 4:1 to 33:1.

22. The microfluidic device as recited in claim 21, wherein the scalable ratio is from 6:1 to 18:1.

23. The microfluidic device as recited in claim 21, including a gasket extending around the perimeter of the micro-channel between the first plate and the second plate, at least one sample port opening extending through the first plate or the second plate, and at least one of the first plate and the second plate includes a recessed well.

24. The microfluidic device as recited in claim 21, wherein the at least one ground electrode includes a grid of wires defining spaces between the wires.

25. A microfluidic device comprising:
a first plate; and
a second plate spaced apart from the first plate such that there is a micro-channel between the first plate and the second plate,
the first plate including a plurality of drive electrodes,
the second plate including an array of electrochemical biosensors, and
one of the first plate and the second plate includes at least one ground electrode operable to establish an electric potential with the plurality of drive electrodes, wherein the at least one ground electrode includes a grid of wires defining spaces between the wires, and wherein each of the electrochemical biosensors is located between the wires in one of the spaces.

* * * * *